United States Patent
Joly et al.

(10) Patent No.: US 11,247,950 B2
(45) Date of Patent: Feb. 15, 2022

(54) APPARATUS AND PROCESS FOR CONVERTING AROMATIC COMPOUNDS BY BENZENE ALKYLATION WITH ETHYLENE

(71) Applicant: IFP Energies Nouvelles, Rueil-Malmaison (FR)

(72) Inventors: Jean-Francois Joly, Rueil-Malmaison (FR); Frederic Feugnet, Rueil-Malmaison (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 17/123,360

(22) Filed: Dec. 16, 2020

(65) Prior Publication Data
US 2021/0179517 A1 Jun. 17, 2021

(30) Foreign Application Priority Data
Dec. 17, 2019 (FR) ........................ 1914578

(51) Int. Cl.
*C07C 7/00* (2006.01)
*B01D 3/14* (2006.01)
(Continued)

(52) U.S. Cl.
CPC .............. *C07C 7/005* (2013.01); *B01D 3/143* (2013.01); *B01D 15/185* (2013.01);
(Continued)

(58) Field of Classification Search
CPC .. C07C 7/005; C07C 7/09; C07C 2/66; C07C 5/2775; C07C 7/04; B01D 15/185; B01D 3/143; B01J 19/245; B01J 2219/0004
See application file for complete search history.

(56) References Cited

U.S. PATENT DOCUMENTS

| | | | |
|---|---|---|---|
| 6,252,126 B1 * | 6/2001 | Netzer | .................. C07C 15/073 585/446 |
| 7,915,471 B2 | 3/2011 | Leflaive et al. | |
| | (Continued) | | |

FOREIGN PATENT DOCUMENTS

FR 3023842 A1 1/2016

OTHER PUBLICATIONS

French Search Report dated Sep. 1, 2020 issued in corresponding FR 1914578 application (2 pages).

*Primary Examiner* — Ali Z Fadhel
(74) *Attorney, Agent, or Firm* — Millen, White, Zelano and Branigan, P.C.; Harry B. Shubin

(57) ABSTRACT

Apparatus and process for converting aromatic compounds, comprising/using: a fractionating train (4-7) suitable for extracting at least one benzene-comprising fraction (22), one toluene-comprising fraction (23) and one fraction (24) comprising xylenes and ethylbenzene from the feedstock (2); a xylene separating unit (10) suitable for treating the fraction comprising xylenes and ethylbenzene and producing a para-xylene-comprising extract (39) and a raffinate (40) comprising ortho-xylene, meta-xylene and ethylbenzene; an isomerizing unit (11) for treating the raffinate and producing a para-xylene-enriched isomerizate (42), which is sent to the fractionating train; and an alkylating reaction section (13) for treating at least part of the benzene-comprising fraction with an ethylene source (30) and producing an alkylation effluent (31) comprising ethylbenzene, which is sent to the isomerizing unit.

15 Claims, 2 Drawing Sheets

(51) Int. Cl.
    *B01D 15/18*     (2006.01)
    *B01J 19/24*     (2006.01)
    *C07C 2/66*     (2006.01)
    *C07C 5/27*     (2006.01)
    *C07C 7/04*     (2006.01)
    *C07C 7/09*     (2006.01)

(52) U.S. Cl.
    CPC ............... *B01J 19/245* (2013.01); *C07C 2/66* (2013.01); *C07C 5/2775* (2013.01); *C07C 7/04* (2013.01); *C07C 7/09* (2013.01); *B01J 2219/0004* (2013.01)

(56) References Cited

U.S. PATENT DOCUMENTS

| | | | |
|---|---|---|---|
| 2015/0251973 A1* | 9/2015 | Tinger | C07C 4/18 585/321 |
| 2017/0073285 A1* | 3/2017 | Whitchurch | C07C 2/64 |
| 2017/0204024 A1 | 7/2017 | Dreux et al. | |

\* cited by examiner

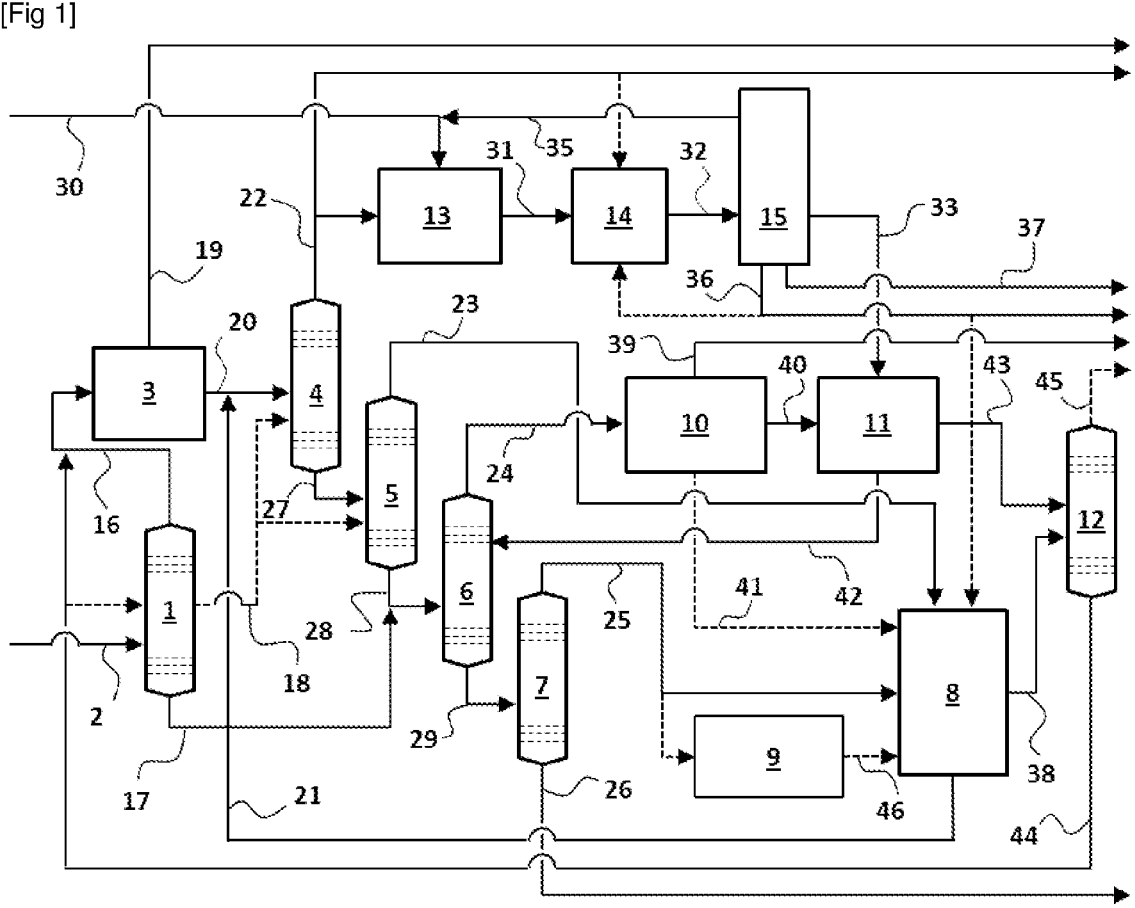
[Fig 1]

[Fig 2]
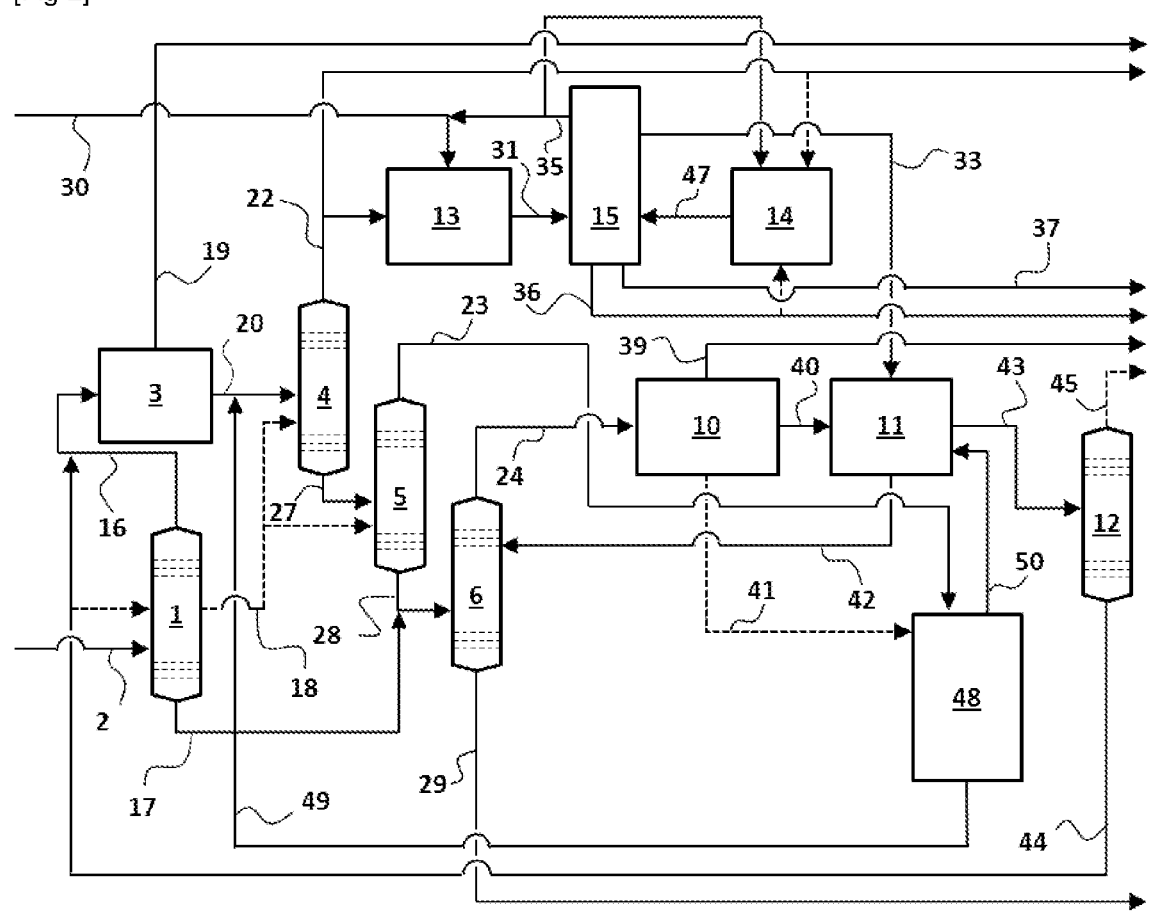

APPARATUS AND PROCESS FOR CONVERTING AROMATIC COMPOUNDS BY BENZENE ALKYLATION WITH ETHYLENE

TECHNICAL FIELD

The invention pertains to the conversion of aromatics in the context of the production of aromatics for petrochemicals (benzene, toluene, para-xylene, ortho-xylene). The object of the invention more particularly is to be able to control the respective amounts of benzene and para-xylene, and in particular to be able to produce only para-xylene.

The aromatic complex (or apparatus for converting aromatic compounds) is supplied with feedstocks composed predominantly of six to ten carbon atoms or more, referred to as C6 to C10+ feedstocks. Various sources of aromatic compounds may be introduced into an aromatic complex, the most widespread of such source being the process in which naphthas are subjected to catalytic reforming. Mixtures of aromatic compounds obtained from a process of converting lignocellulosic biomass may also be introduced, after a purification treatment, into an aromatic complex. The process of catalytic pyrolysis of lignocellulosic biomass, for example, may be considered as a source of aromatics.

Within an aromatic complex, irrespective of the source of aromatics, benzene and alkylaromatics (e.g. toluene, para-xylene, ortho-xylene) are extracted therefrom and then converted into desired intermediates. The products of interest are aromatics having 0 (benzene), 1 (toluene) or 2 (xylenes) methyl groups, and more particularly, among the xylenes, para-xylene, which has the greatest market value.

It is therefore appropriate to dispose methyl groups in such a way that all of the aromatic ring systems exiting the aromatic complex possess two methyl groups (e.g. para-xylene, ortho-xylene).

PRIOR ART

To date, aromatic complexes make it possible to produce benzene, optionally toluene, and xylenes (often para-xylene, sometimes ortho-xylene). An aromatic complex generally possesses at least one catalytic unit having at least one of the following functions:
- isomerizing aromatic compounds having eight carbon atoms referred to as A8 compounds, which allows ortho-xylene, meta-xylene and ethylbenzene to be converted into para-xylene;
- transalkylation, which allows xylenes to be produced from a mixture of toluene (and optionally of benzene) and of A9+ compounds such as trimethylbenzenes and tetramethylbenzenes; and
- disproportionation of the toluene, which allows the production of benzene and of xylenes.

The aromatic group allows production of high-purity para-xylene via separation by adsorption or by crystallization, an operation which is well known in the prior art. This "C8 aromatic loop" includes a step of removing the heavy compounds (i.e., C9+) in a distillation column which is called the "xylenes column". The overhead flow from this column, which contains the C8 aromatic isomers (i.e., A8), is then sent into the para-xylene separation process, which is, very generally, a process for separation by simulated moving bed (SMB) adsorption, to produce an extract and a raffinate, or a crystallization process, in which a para-xylene fraction is isolated from the rest of the constituents of the mixture in the form of crystals.

The extract, which contains the para-xylene, is then distilled to give the high-purity para-xylene. The raffinate, which is rich in meta-xylene, ortho-xylene and ethylbenzene, is treated in a catalytic isomerizing unit, which returns a mixture of C8 aromatics in which the proportion of xylenes (ortho-, meta-, para-xylenes) is virtually at thermodynamic equilibrium and the amount of ethylbenzene is reduced. This mixture is again sent into the "xylenes column" with the fresh feedstock.

All of the industrial processes for isomerizing C8 aromatics enable the isomerization of xylenes. The conversion of the ethylbenzene, on the other hand, is dependent on the type of process and of catalyst that are selected. The reason is that petrochemical complexes utilize either an "isomerizing" isomerizing unit (i.e. isomerization of ethylbenzene into a mixture of C8 aromatics) or a "dealkylating" isomerizing unit (i.e., dealkylation of ethylbenzene into benzene), in order to promote the production (at the exit from the aromatic loop) respectively either of para-xylene alone or of benzene and para-xylene.

The selection of an "isomerizing" isomerization makes it possible, as indicated above, to maximize the production of para-xylene, which is the compound having the highest added value at the exit from the aromatic complex. The combination of an "isomerizing" isomerization and a liquid-phase isomerization within an aromatic complex, as described for example in U.S. Pat. Nos. 8,697,929, 7,371,913, 4,962,258, 6,180,550, 7,915,471, U.S. Ser. No. 10/035,739 and U.S. Ser. No. 10/029,958, makes it possible in particular to maximise the amount of para-xylene produced while reducing the loss of aromatic rings, relative to a prior-art aromatic complex.

SUMMARY OF THE INVENTION

In the context described above, a first object of the present invention is to overcome the problems of the prior art and to provide an apparatus and a process for producing aromatics for petrochemicals that allow the respective amounts of benzene and para-xylene to be adjusted for any type of feedstock supplied to an aromatic complex, or even of producing only para-xylene. The subject of the invention also makes it possible to increase the amounts of aromatics produced.

The invention resides in the introduction of ethylene into the aromatic complex and in the provision of one or more units which enable the ethylene to be converted and, in particular, which enable only para-xylene to be produced. Specifically, the subject of the present invention may be summarized as the addition of a catalytic unit to the aromatic complex, this catalytic unit enabling benzene to be converted into ethylbenzene by reaction of benzene with ethylene. This unit comprises an alkylated reaction section which produces ethylbenzene. An optional transalkylating reaction section may also allow the polyethylbenzenes, which are possible by-products of the alkylation reaction of benzene with ethylene, to be converted into ethylbenzenes. The ethylbenzene thus produced is converted into para-xylene in the aromatic loop of the aromatic complex.

According to a first aspect, the aforementioned objects, and also other advantages, are obtained by an apparatus for converting a feedstock of aromatic compounds, comprising:
   a fractionating train suitable for extracting at least one fraction comprising benzene, one fraction comprising toluene and one fraction comprising xylenes and ethylbenzene from the feedstock;

a xylene separating unit suitable for treating the fraction comprising xylenes and ethylbenzene and for producing an extract comprising para-xylene and a raffinate comprising ortho-xylene, meta-xylene and ethylbenzene;

an isomerizing unit suitable for treating the raffinate and producing a para-xylene-enriched isomerizate, which is sent to the fractionating train; and an alkylating reaction section suitable for treating at least part of the benzene-comprising fraction with a source of ethylene and producing an alkylating effluent comprising ethylbenzene, which is sent to the isomerizing unit.

According to one or more embodiments, the device further comprises a transalkylating reaction section suitable for transalkylating polyethylbenzenes present in the alkylation effluent and producing an ethylbenzene-enriched fraction.

According to one or more embodiments, the device further comprises a fractionating unit suitable for treating the alkylation effluent and producing a plurality of fractionation fractions comprising at least one ethylbenzene fraction, which is sent to the isomerizing unit, and one benzene fraction.

According to one or more embodiments, the fractionating unit is disposed downstream of the transalkylated reaction section and is suitable for treating the ethylbenzene-enriched fraction.

According to one or more embodiments, the fractionating unit is suitable for producing additionally at least one polyethylbenzene fraction, and the transalkylating reaction section is disposed downstream of the fractionating unit and is suitable for treating at least part of said polyethylbenzene fraction.

According to one or more embodiments, the fractionating train is suitable for extracting a C9-C10 monoaromatics fraction from the feedstock.

According to one or more embodiments, the device further comprises a transalkylating unit suitable for treating the C9-C10 monoaromatics fraction with the toluene-comprising fraction and producing xylenes, which are sent to the fractionating train.

According to one or more embodiments, the device further comprises a disproportionating unit suitable for treating at least partly the toluene-comprising fraction and producing a xylene-enriched fraction, which is recycled to the isomerizing unit.

According to a second aspect, the aforementioned objects, and also other advantages, are obtained by a process for converting a feedstock of aromatic compounds, comprising the following steps:

fractionating the feedstock in a fractionating train to extract at least one benzene-comprising fraction, one toluene-comprising fraction and one fraction comprising xylenes and ethylbenzenes;

separating the fraction comprising xylenes and ethylbenzene in a xylene separating unit and producing a para-xylene-comprising extract and a raffinate comprising ortho-xylene, meta-xylene and ethylbenzene;

isomerizing the raffinate in an isomerizing unit and producing a para-xylene-enriched isomerizate;

sending the para-xylene-enriched isomerizate to the fractionating train;

alkylating at least part of the benzene-comprising fraction with an ethylene source in an alkylating reaction section and producing an alkylation effluent comprising ethylbenzene; and sending the alkylation effluent comprising ethylbenzene to the isomerizing unit.

According to one or more embodiments, the alkylated reaction section comprises at least one alkylating reactor, which is used under the following operating conditions:
 temperature of between 20° C. and 400° C.;
 pressure of between 1 and 10 MPa;
 molar benzene/ethylene ratio of between 2 and 10;
 WWH of between 0.5 and 50 $h^{-1}$.

According to one or more embodiments, the alkylated reactor is operated in the presence of catalysts comprising a zeolite.

According to one or more embodiments, the isomerizing unit comprises a gas-phase isomerization zone and/or a liquid-phase isomerization zone, wherein the gas-phase isomerization zone is used under the following operating conditions:
 temperature of greater than 300° C.;
 pressure of less than 4.0 MPa;
 hourly space velocity of less than 10 $h^{-1}$;
 molar hydrogen-to-hydrocarbon ratio of less than 10;
 in the presence of a catalyst comprising at least one zeolite having channels whose opening is defined by a ring of 10 or 12 oxygen atoms, and at least one group VIII metal in an amount of between 0.1 and 0.3 weight %, endpoints included, and wherein the liquid-phase isomerization zone is used under the following operating conditions:
 temperature of less than 300° C.;
 pressure of less than 4 MPa;
 hourly space velocity of less than 10 $h^{-1}$;
 in the presence of a catalyst comprising at least one zeolite having channels whose opening is defined by a ring of 10 or 12 oxygen atoms.

According to one or more embodiments, the process further comprises the following step:
 transalkylating polyethylbenzenes present in the alkylation effluent in a transalkylating reaction section and producing an ethylbenzene-enriched fraction, and
 sending the ethylbenzene-enriched fraction to the isomerizing unit.

According to one or more embodiments, the transalkylating reaction section comprises at least one transalkylation reactor, which is used under the following operating conditions:
 temperature of between 200° C. and 400° C.;
 pressure of between 1 and 6 MPa;
 WWH of between 0.5 and 5 $h^{-1}$.

According to one or more embodiments, the transalkylation reactor is operated in the presence of a catalyst comprising a zeolite.

Embodiments according to the first aspect and the second aspect, and also other characteristics and advantages of the apparatuses and processes according to the abovementioned aspects, will become apparent on reading the description which follows, which is given solely by way of illustration and without limitation, and with reference to the drawings which follow.

LIST OF FIGURES

FIG. 1 shows a schematic view of a process according to the present invention, enabling an increase in the production of para-xylene.

FIG. 2 shows a schematic view of a process according to the present invention, enabling an increase in the production of para-xylene, in which the transalkylating unit is replaced with a disproportionating unit, and in which the transalkylating reaction section is disposed downstream of the fractionating unit.

DESCRIPTION OF THE EMBODIMENTS

Embodiments of the device according to the first aspect and of the process according to the second aspect will now be described in detail. In the detailed description below, numerous specific details are set out in order to convey a deeper understanding of the apparatus. However, it will be apparent to the skilled person that the apparatus can be employed without these specific details. In other cases, characteristics which are well known have not been described in detail, in order not to complicate the description to no purpose.

In the present specification, the term "comprise" is synonymous with (signifies the same thing as) "include" and "contain", and is inclusive or open, and does not exclude other elements which are not stated. It is understood that the term "comprise" includes the exclusive and closed term "consist". Moreover, in the present description, an effluent comprising essentially or solely compounds A corresponds to an effluent comprising at least 80 or 90 weight %, preferably at least 95 weight %, very preferably at least 99 weight % of compounds A.

The present invention may be defined as an apparatus and a process comprising a sequence of unitary operations which enable the production either of para-xylene exclusively or of para-xylene and benzene.

The apparatus and the process according to the invention are characterized in that in that they comprise and use the catalytic units and the separating units that are known to the skilled person for producing benzene and para-xylene, these units being commonly encountered in aromatic complexes, and in that they comprise and use a reaction section for alkylating benzene using ethylene, and optionally a reaction section for transalkylating polyethylbenzene by-products. Said reaction section for alkylating benzene with ethylene produces ethylbenzene. One of the characteristics of the present invention is the selective conversion of this ethylbenzene, obtained by alkylation, within a unit for isomerizing aromatic C8 compounds, said isomerizing unit treating aromatic compounds of the aromatic complex with the addition of the ethylbenzene produced by alkylating benzene with ethylene.

Surprisingly, the combination of the reaction section for alkylating benzene with ethylene, and of the isomerizing unit, enables not only an increase in the amount of aromatics produced but also the possibility of obtaining only para-xylene.

Referring to FIG. 1, according to one or more embodiments, the apparatus for converting the aromatic compounds comprises:
  an optional feedstock separating unit 1 for separating the entering feedstock 2 for the aromatic complex into a 7 carbon atoms or fewer (C7-) hydrocarbon fraction and an 8 carbon atoms or more (A8+) aromatic fraction;
  an optional aromatics extraction unit 3 between the feedstock separating unit 1 and a fractionated train 4-7, for separating the aliphatic compounds from the benzene and the toluene in the C7- fraction of the feedstock for the complex;
  the fractionating train 4-7 downstream of the optional aromatics extraction unit 3, enabling the extraction of the benzene, the toluene and the xylenes from the other aromatics;
  an optional transalkylating unit 8, which converts the toluene (and optionally the benzene) and methylalkylbenzenes such a trimethylbenzenes into xylenes—advantageously this unit may also treat tetramethylbenzenes;
  an optional selective hydrogenolysis unit 9 suitable for treating a fraction comprising aromatic compounds having 9 and 10 carbon atoms, and producing a hydrogenolysis effluent which is enriched in methyl-substituted aromatic compounds;
  an optional separating unit (not shown) for separating the hydrogenolysis effluent disposed (e.g., directly) downstream of the selective hydrogenolysis unit 9, for producing a plurality of liquid effluent fractions;
  a xylene separating unit 10 (e.g., a crystallization unit or simulated moving bed unit employing a molecular sieve and a desorbent such as toluene), which enables the para-xylene to be isolated from the xylenes and the ethylbenzene;
  a unit 11 for isomerizing the raffinate obtained as effluent from the xylene separating unit 10, for conversion in particular of the ortho-xylene, meta-xylene and ethylbenzene into para-xylene;
  an optional stabilizing column 12, which enables in particular the withdrawal of the more volatile species (e.g., C5-) from the aromatic complex, especially the effluents from the transalkylating unit 8 and/or the isomerizing unit 11;
  an alkylating reaction section 13 for alkylating a benzene-comprising fraction with ethylene and producing ethylbenzene;
  an optional transalkylating section 14, for transalkylating the polyethylbenzenes obtained from the alkylating reaction section 13 and producing an ethylbenzene-enriched effluent;
  a fractionating unit 15 for separating the alkylation products, disposed downstream of the alkylating reaction section 13.

Advantageously, the alkylating reaction section 13 enables the production of a surplus of aromatics by the addition of ethylene (adding two carbon atoms to each molecule of benzene), and provides the possibility of being able to convert the entirety of the benzene into para-xylene. Furthermore, the small amount of heavy compounds obtained from the section of alkylating benzene with ethylene, this amount not being used for transalkylation with the benzene, may be utilized as fuel (e.g., kerosene or gas-oil).

Referring to FIG. 1, the feedstock separating unit 1 treats the feedstock 2 entering the aromatic complex, to separate an overhead fraction 16 comprising (e.g., essentially) compounds having 7 carbon atoms or fewer (C7-), containing, in particular benzene and toluene, and a bottom fraction 17 comprising (e.g., essentially) aromatics having 8 carbon atoms or more (A8+), which is sent to the xylene column 6. According to one or more embodiments, the feedstock separating unit 1 also separates a first toluene fraction 18 comprising at least 90 weight %, preferably at least 95 weight %, very preferably at least 99 weight % of toluene. According to one or more embodiments, the first toluene fraction 18 is sent to the first column 4 for distilling aromatic compounds, also referred to as the benzene column, and/or to the second column 5 for distilling aromatic compounds, also referred to as the toluene column.

According to one or more embodiments, the entering feedstock 2 is a hydrocarbon fraction containing predominantly (i.e., >50 weight %) molecules whose carbon number is from 6 to 10 carbon atoms. This feedstock may also contain molecules having more than 10 carbon atoms and/or molecules having 5 carbon atoms.

The feedstock 2 entering the aromatic complex is rich in aromatics (e.g. >50 weight %) and contains preferably at least 1 weight % of benzene, more preferably at least 5 weight %, very preferably at least 10 weight % of benzene. The entering feedstock 2 may be produced by catalytic reforming of a naphtha, or may be a product of a cracking unit (e.g., steam cracking, catalytic cracking), or of any other means for producing alkylaromatics.

According to one or more embodiments, the entering feedstock 2 comprises less than 10 ppm by weight, preferably less than 5 ppm by weight, very preferably less than 1 ppm by weight of elemental nitrogen, and/or less than 10 ppm by weight, preferably less than 5 ppm by weight, very preferably less than 1 ppm by weight of elemental sulfur, and/or less than 100 ppm by weight, preferably less than 50 ppm, very preferably less than 10 ppm by weight of elemental oxygen.

The overhead fraction 16 from the feedstock separating unit 1, optionally mixed with the bottom product (benzene and toluene) from the stabilizing column 12, which will be defined hereinafter, is sent to the aromatics extraction unit 3 for the extraction of an effluent 19 comprising C6-C7 19 aliphatic species, which is exported as a co-product of the aromatic complex. The fraction called aromatic fraction 20 (essentially benzene and toluene) which is extracted from the aromatics extraction unit 3, optionally mixed with the heavy fraction 21 from the transalkylating unit 8, which will be defined hereinafter, is sent to the benzene column 4. According to one or more embodiments, the aromatic fraction 20 is a C6-C7 aromatic (A6-A7) hydrocarbon (e.g., essentially) feedstock.

According to one or more embodiments, the fractionated train comprises the columns 4, 5, 6 and 7 for distilling aromatic compounds, enabling the separation of the following five fractions:
  a fraction 22 comprising (e.g., essentially) benzene;
  a fraction 23 comprising (e.g., essentially) toluene;
  a fraction 24 comprising (e.g., essentially) xylenes and ethylbenzene;
  a fraction 25 comprising (e.g., essentially) aromatic compounds having 9 and 10 carbon atoms;
  a fraction 26 comprising (e.g., essentially) aromatic compounds, in which the most volatile species are aromatics having 10 carbon atoms.

The benzene column 4 is suitable for: treating the aromatic fraction 20, which is a C6-C10 (e.g., essentially) aromatic hydrocarbon feedstock (A6+); producing at the top the benzene-comprising fraction 22, which may be one of the desired products exiting the aromatic complex; and producing at the bottom a C7-C10 (e.g., essentially) aromatic effluent 27 (A7+).

The toluene column 5 is suitable for: treating the C7–010 aromatic effluent 27 (A7+), the bottom product from the benzene column 4; producing at the top the toluene-comprising fraction 23, which is passed to the transalkylating unit 8; and producing at the bottom a C8-C10 (e.g., essentially) aromatic effluent 28 (A8+).

The third distillation column, 6, for aromatic compounds, also referred to as the xylene column, is suitable for: treating the aromatic fraction 17 having 8 or more carbon atoms (A8+) of the feedstock of the aromatic complex and optionally the bottom effluent 28 from the toluene column; producing at the top the fraction 24 comprising xylenes and ethylbenzene, which is passed to the xylenes separating unit 10; and producing at the bottom an effluent 29 (e.g., essentially) comprising C9-C10 aromatics (A9+).

The fourth distillation column, 7, for aromatic compounds, also referred to as the heavy aromatics column, is optional and is suitable for: treating the bottom effluent 29 from the xylene column; producing at the top the fraction 25 comprising C9-C10 monoaromatics; and producing at the bottom the fraction 26 comprising (e.g., essentially) aromatic compounds of which the more volatile species are aromatics having 10 carbon atoms (A10+). The bottom fraction 26 preferably comprises C11+ compounds.

Obtained at the top of the benzene column 4 is the benzene-comprising fraction 22, which is sent at least partly to the alkylating reaction section 13 for reaction with an ethylene source 30 to produce an alkylation effluent 31 comprising ethylbenzene and potentially benzene and/or polyethylbenzenes (by-products). According to one or more embodiments, the alkylating reaction section 13 is fed with a mixture consisting (e.g., essentially) of benzene and of ethylene. According to one or more embodiments, the alkylation effluent 31 comprises at least 5 weight %, preferably at least 8 weight %, very preferably at least 10 weight % of ethylbenzene. The balance to 100 is composed primarily (e.g. >50 weight %), or even essentially, of benzene, the latter being generally used in excess.

According to one or more embodiments, the alkylating reaction section 13 comprises at least one alkylation reactor suitable for use under at least one of the following operating conditions:
  temperature of between 20° C. and 400° C., preferably between 150° C. and 400° C., and more preferably still of between 220° C. and 300° C.;
  pressure of between 1 and 10 MPa, preferably of between 2 and 7 MPa, and more preferably of between 3 and 5 MPa;
  molar benzene/ethylene ratio of between 2 and 10, and preferably between 4 and 8;
  WWH of between 0.5 and 50 $h^{-1}$, preferably of between 1 and 10 $h^{-1}$, and more preferably of between 1.5 and 3 $h^{-1}$.

The term WWH corresponds to the hourly weight of hydrocarbon feedstock injected, based on the weight of catalyst charged.

According to one or more embodiments, the alkylating reactor is operated in the presence of a catalyst comprising a zeolite. According to one or more embodiments, the zeolite-based catalyst, based preferably on zeolite Y and very preferably on dealuminated zeolite Y, comprises from 1 to 100 weight %, preferably 20 to 98 weight %, for example 40 to 98 weight % of said zeolite and 0 to 99 weight %, preferably 2 to 80 weight % and, for example, 2 to 60 weight % of a matrix. According to one or more embodiments, the catalyst comprises a dealuminated zeolite Y having an overall atomic Si/Al ratio of more than 4, preferably between 8 and 70, and preferably containing no extra-framework aluminous species. Said dealuminated zeolite Y may be employed alone or in a mixture with a binder or a matrix, generally selected from the group consisting of clays, aluminas, silica, magnesium, zirconia, titanium oxide, boron oxide, and any combination of at least two of these oxides, such as silica-alumina and silica-magnesium. Any of the known methods for agglomeration and shaping are applicable, such as, for example, extrusion, pelletization or droplet coagulation. Zeolites such as the dealuminated zeolites Y and their preparation are well known. Reference may be made, for example, to U.S. Pat. No. 4,738,940.

According to one or more embodiments, the alkylating reactor is a fixed bed reactor.

According to one or more embodiments, the alkylation effluent 31 is transalkylated in the optional transalkylating section 14 to produce an ethylbenzene-enriched fraction 32. According to one or more embodiments, the transalkylating reaction section 14 is fed with benzene, for example when an excess of ethyl groups is observed in the alkylation effluent 31 for producing ethylbenzene.

According to one or more embodiments, the ethylbenzene-enriched fraction 32 is sent to the fractionating unit 15 to produce an ethylbenzene fraction 33, a benzene fraction 35, which may, for example, be at least partly recycled to the alkylating reaction section 13, and optionally one or more polyethylbenzene fractions 36 and 37. According to one or more embodiments, the ethylbenzene fraction 33 is fed to the isomerizing unit 11. In this way, all of the ethylbenzene, present initially in the feedstock and produced by alkylation in the alkylating reaction section 13, is introduced and converted into para-xylene in the aromatic loop containing the isomerizing unit 11 and the xylenes separating unit 10.

According to one or more embodiments, the alkylation effluent 31 is sent directly to the fractionating unit 15.

According to one or more embodiments, the fractionating unit 15 comprises a series of fractionating columns (e.g., series of three columns) which is suitable for extracting the benzene fraction 35 (for example at the top of the first fractionating column, the ethylbenzene fraction 33 (for example at the top of the second fractionating column), a first polyethylbenzene fraction 36 comprising diethylbenzene and optionally triethylbenzene (for example at the top of the third fractionating column), and a second polyethylbenzene fraction 37 comprising, in particular, tetraethylbenzene (for example at the bottom of the third fractionating column).

According to one or more embodiments, the first polyethylbenzenes fraction 36 is at least partly recycled to the transalkylating reaction section 14. According to one or more embodiments, the first polyethylbenzenes fraction 36 is at least partly recycled to the transalkylating unit 8. According to one or more embodiments, the second polyethylbenzenes fraction 37, called the tar fraction or heavy fraction, is withdrawn from the aromatic complex. According to one or more embodiments, the second polyethylbenzenes fraction 37 is evacuated with the bottom fraction 26 from the heavy aromatics column 7.

In the transalkylating unit 8, the fraction 25 comprising C9-C10 monoaromatics (and/or the hydrogenolysis effluent enriched in methyl-substituted aromatic compounds, described hereinafter) is mixed with the toluene-comprising fraction 23 coming from the top of the toluene column 5, and is used to feed the reaction section of the transalkylating unit 8, to produce xylenes by transalkylation of aromatics with a deficit of methyl groups (toluene) and aromatics with an excess of methyl groups (e.g., tri- and tetramethylbenzenes). According to one or more embodiments, the transalkylating unit 8 is fed with benzene (line not shown in FIG. 1), for example when an excess of methyl groups is observed, for the production of para-xylene.

According to one or more embodiments, the transalkylating unit 8 comprises at least one first transalkylating reactor suitable for use under at least one of the following operating conditions:

temperature of between 200° C. and 600° C., preferably of between 350° C. and 550° C., and more preferably still of between 380° C. and 500° C.;

pressure of between 2 and 10 MPa, preferably of between 2 and 6 MPa, and more preferably of between 2 and 4 MPa;

WWH of between 0.5 and 5 $h^{-1}$, preferably of between 1 and 4 $h^{-1}$, and more preferably of between 2 and 3 $h^{-1}$.

According to one or more embodiments, the first transalkylating reactor is operated in the presence of a catalyst comprising zeolite, for example ZSM-5. According to one or more embodiments, the second transalkylating reactor is a fixed bed reactor.

According to one or more embodiments, the transalkylating reaction section 14 comprises at least one second transalkylating reactor which is suitable for use under at least one of the following operating conditions:

temperature of between 200° C. and 400° C., preferably of between 220° C. and 350° C., and more preferably still of between 250° C. and 310° C.;

pressure of between 1 and 6 MPa, preferably of between 2 and 5 MPa, and more preferably of between 3 and 5 MPa;

WWH of between 0.5 and 5 $h^{-1}$, preferably of between 0.5 and 4 $h^{-1}$, and more preferably of between 0.5 and 3 $h^{-1}$.

According to one or more embodiments, the second transalkylating reactor is operated in the presence of a catalyst comprising zeolite, for example dealuminated zeolite Y (for example, a zeolite similar to those described in the alkylating catalyst part). According to one or more embodiments, the second transalkylating reactor is a fixed bed reactor.

According to one or more embodiments, the effluents from the reaction section of the transalkylating unit 8 are separated in a first separation column (not shown) downstream of said reaction section of the transalkylating unit 8. A fraction 38 comprising at least some of the benzene and the more volatile species (C6−) is extracted at the top of the first separating column and is sent to an optional stabilizing column 12, enabling the removal in particular of the more volatile species (e.g., C5−) from the aromatic complex. The heavy fraction 21 of the effluents from the first separating column, comprising (e.g., essentially) aromatics having at least 7 carbon atoms (A7+), is optionally recycled to the fractionating train 4-7, for example to the benzene column 4.

The fraction 24 comprising xylenes and ethylbenzene is treated in the xylenes separating unit 10 to produce a fraction or extract 39 comprising para-xylene, and a raffinate 40. The extract 39 may be subsequently distilled (e.g., in the case of separation by adsorption SMB), for example by means of an extract column and then a further toluene column (which are not shown), if toluene is used as a desorbent, in order to obtain high-purity para-xylene, which is exported as a principal product. The raffinate 40 from the xylenes separating unit 10 comprises (e.g., essentially) ortho-xylene, meta-xylene and ethylbenzene, and is used to feed the isomerizing unit 11.

According to one or more embodiments, the xylenes separating unit 10 also separates a second toluene fraction 41, which comprises at least 90 weight %, preferably at least 95 weight % and very preferably at least 99 weight % of toluene. The toluene fraction 41 may be, for example, a part of the toluene which is used as a desorbent, when the xylenes separating unit 10 comprises a simulated moving bed adsorption unit. According to one or more embodiments, the second toluene fraction 41 is sent to the transalkylating unit 8.

In the isomerization reaction section (not shown) of the isomerizing unit 11, the isomers of para-xylene are isomerized, whereas the ethylbenzene may be: isomerized to give a mixture of C8 aromatics, for example if the aim is to produce primarily para-xylene; and/or dealkylated to produce benzene, for example if the aim is to produce both paraxylene and benzene. According to one or more embodiments, the effluents from the isomerization reaction section are sent to a second separation column (not shown) to produce, at the bottom, a para-xylene enriched isomerizate 42, which is preferably recycled to the xylene column 6; and to produce, at the top, a hydrocarbon fraction 43 comprising compounds having 7 or fewer carbon atoms (C7−), which is sent to the optional stabilizing column 12, for example with the fraction comprising at least part of the benzene, and the more volatile species 38.

According to one or more embodiments, the isomerizing unit 11 comprises a first isomerization zone which works in liquid phase, and/or a second isomerizing zone which works in gaseous phase, as is described in the patents referenced earlier. According to one or more embodiments, the isomerizing unit 11 comprises a first isomerizing zone, which works in liquid phase, and a second isomerizing zone, which works in gaseous phase. According to one or more embodiments, a first part of the raffinate 40 is sent to the liquid-phase isomerizing unit, to give a first isomerizate, which is used to feed, directly and at least partly, the separating unit 10; and a second part of the raffinate 40 is sent to the gaseous-phase isomerizing unit, to give an isomerizate which is sent to the xylene column 6. According to one or more embodiments, the ethylbenzene fraction 33 is sent on a majority basis (i.e., at least 50%, e.g., at least 60%, preferably at least 70%) into the first isomerizing zone, working in gaseous phase, to be preferentially isomerized to para-xylene.

Advantageously, the isomerizing unit 11 enables the surplus ethylbenzene provided by the alkylating reaction section 13 to be converted with a very high selectivity.

According to one or more embodiments, the gaseous-phase isomerizing zone is suitable for use under at least one of the following operating conditions:
- temperature greater than 300° C., preferably from 350° C. to 480° C.;
- pressure of less than 4.0 MPa, and preferably from 0.5 to 2.0 MPa;
- hourly space velocity (HSV) less than 10 h$^{-1}$ (10 litres per litre per hour), preferably between 0.5 h$^{-1}$ and 6 h$^{-1}$;
- molar ratio of hydrogen to hydrocarbon of less than 10, and preferably of between 3 and 6;
- in the presence of a catalyst comprising at least one zeolite having pores whose opening is defined by a ring of 10 or 12 oxygen atoms (10 MR or 12 MR), and at least one group VIII metal with a content of between 0.1 and 0.3 weight % (reduced form), endpoints included.

According to one or more embodiments, the liquid phase isomerizing zone is suitable for use under at least one of the following operating conditions:
- temperature of less than 300° C., preferably 200° C. to 260° C.;
- pressure of less than 4 MPa, preferably 2 to 3 MPa;
- hourly space velocity (HSV) of less than 10 h$^{-1}$ (10 litres per litre per hour), preferably between 2 and 4 h$^{-1}$;
- in the presence of a catalyst comprising at least one zeolite having pores whose opening is defined by a ring of 10 or 12 oxygen atoms (10 MR or 12 MR), preferably a catalyst comprising at least one zeolite having pores whose opening is defined by a ring of 10 oxygen atoms (10 MR), and more preferably a catalyst comprising a ZSM-5 zeolite.

The term HSV corresponds to the hourly volume of hydrocarbon feedstock projected, relative to the volume of catalyst charged.

According to one or more embodiments, the optional stabilizing column 12 produces: at the bottom, a stabilized fraction 44 comprising (e.g., essentially) benzene and toluene, which is optionally recycled to the entrance of the feedstock separating unit 1 and/or of the aromatics extracting unit 3; and, at the top, a fraction 45 of more volatile species (e.g., C5−), which is removed from the aromatic complex.

According to one or more embodiments, the selective hydrogenolysing unit 9 is suitable for:
- treating the monoaromatics 25 having between 9 and 10 carbon atoms; and
- producing a hydrogenolysis effluent 46 enriched in methyl-substituted aromatic compounds.

Specifically, the selective hydrogenolysing unit 9 may be suitable for treating aromatics 25 having between 9 and 10 carbon atoms, by converting one or more alkyl groups having at least two carbon atoms (ethyl, propyl, butyl, isopropyl groups, etc.) attached to a benzene ring into one or more methyl groups, i.e., groups formed of a single $CH_3$ group. The major advantage of the selective hydrogenolysing unit 9 is that of increasing the $CH_3$ groups content and lowering the content of ethyl, propyl, butyl, isopropyl groups, etc., in the feedstock of the isomerizing unit 11, in order to increase the production rate of xylenes, and especially of para-xylene, in said isomerizing unit 11.

According to one or more embodiments, the selective hydrogenolysing unit 9 comprises at least one hydrogenolysis reactor which is suitable for use under at least one of the following operating conditions:
- temperature of between 300° C. and 550° C., preferably of between 350° C. and 500° C., and more preferably still of between 370° C. and 450°;
- pressure of between 0.1 and 3 MPa, preferably of between 0.2 and 2 MPa, and more preferably of between 0.2 and 1 MPa;
- molar $H_2$/HC (hydrocarbon feedstock) ratio of between 1 and 10, and preferably of between 1.5 and 6;
- WWH of between 0.1 and 50 h$^{-1}$ (e.g., 0.5-50 h$^{-1}$), preferably of between 0.5 and 30 h$^{-1}$ (e.g., 1-30 h$^{-1}$), and more preferably of between 1 and 20 h$^{-1}$ (e.g., 2-20 h$^{-1}$, 5-20 h$^{-1}$).

According to one or more embodiments, the hydrogenolysis reactor is operated in the presence of a catalyst comprising at least one metal from group VIII of the Periodic Table, preferably nickel and/or cobalt, deposited on a porous support comprising at least one crystalline or non-crystalline refractory oxide having or not having a structured porosity.

According to one or more embodiments, the metal from group VIII is nickel. The presence of a promoter (group VIB VIIB VIII IB IIB) is also possible. The catalyst is supported on a refractory oxide (e.g., alumina or silica), which has optionally been neutralized by treatment with a base.

According to one or more embodiments, the hydrogenolysis reactor is a fixed bed reactor and the catalyst support takes the form of extra beds. According to one or more embodiments, the hydrogenolysis reactor is a moving bed reactor, and the catalyst support takes the form of approximately spherical beads. A moving bed may be defined as being a gravity flow bed, such as those encountered in the catalytic reforming of gasolines.

FIG. 2 represents a schematic view of a process according to the present invention, enabling the production of para-xylene to be increased, where the transalkylating reaction section 14 is disposed downstream of the fractionating unit 15. According to one or more embodiments, the alkylation effluent 31 is separated in the fractionating unit 15 to produce the ethylbenzene fraction 33, the benzene fraction 35, which may, for example, be recycled at least partly to the alkylating reaction section 13 and/or the transalkylating reaction section 14, and optionally one or more polyethylbenzene fractions 36 and 37. The ethylbenzene fraction 33 is used to feed the isomerizing unit 11.

Still referring to FIG. 2, according to one or more embodiments, at least a portion of the first polyethylbenzenes fraction 36 is sent to the transalkylating reaction section 14, to produce an ethylbenzene-enriched fraction 47, which is returned to the fractionating unit 15. According to one or more embodiments, the transalkylation zone 14 is at least partly fed with at least a portion of the benzene fraction 35 coming from the fractionating section 15.

The apparatus and the process for converting aromatic compounds as described above comprise a transalkylating unit 8, which enables conversion of the toluene and/or benzene into xylenes, using methylbenzenes. It is appreciated that the apparatus and the process for converting aromatic compounds may comprise a disproportionation unit in combination with or in substitution of the transalkylating unit 8, with the disproportionation unit allowing toluene to be converted into benzene and xylene. For example, referring to FIG. 2, when a disproportionation unit 48 is used in place of the transalkylating unit 8, the bottom effluent 29 from the xylene column 6 may be evacuated from the aromatic complex (omission of the heavy aromatics column 7 and the selective hydrogenolysis unit 9 which are present in FIG. 1).

According to one or more embodiments, the effluents from the reaction section of the disproportionation unit 48 are separated in a third separating column (not shown) downstream of said reaction section of the disproportionation unit 48, to produce: a xylene-enriched fraction (50), which is preferably recycled to the isomerizing unit 11; and to produce a benzene and toluene fraction 49, which is preferably sent to the benzene column 4.

Referring to FIGS. 1 and 2, the apparatus and the process for converting aromatic compounds as described above are suitable for sending the first toluene fraction 18 to the benzene column 4, and/or the toluene column 5, and for sending the second toluene fraction 41 to the transalkylating unit 8 or the disproportionation unit 48. It would be appreciated that the apparatus and the process for converting aromatic compounds may be made suitable for sending the first toluene fraction 18 to the transalkylating unit 8 or the disproportionation unit 48, and/or for sending second toluene fraction 41 to the benzene column 4, and/or the toluene column 5.

The apparatus and the process according to the invention therefore enable gains of up to 100% in terms of para-xylene to be obtained, when the entirety of the benzene is alkylated using the ethylene.

In the present specification, the groups of chemical elements are given, unless otherwise specified, according to the CAS classification (CRC Handbook of Chemistry and Physics, published by CRC Press, Editor in Chief D. R. Lide, 81st edition, 2000-2001). For example, group VIII according to the CAS classification corresponds to the metals from columns 8, 9 and 10 according to the new IUPAC classification; group VIb according to the CAS classification corresponds to the metals from column 6 according to the new IUPAC classification.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 1914578, filed Dec. 17, 2019 are incorporated by reference herein.

EXAMPLES

Reference Apparatus Example

A reference apparatus example is used for converting a feedstock comprising a mixture of aromatic compounds obtained from a lignocellulosic biomass conversion process based on conversion by catalytic pyrolysis.

The reference apparatus example is similar to the apparatus represented in FIG. 1.

However, the reference apparatus example does not employ the following units:
  selective hydrogenolysing unit 9;
  stabilizing column 12;
  alkylating reaction section 13;
  transalkylating reaction section 14; and
  fractionating unit 15.

The flow rates of said aromatic compounds of the feedstock to be treated, at the entrance of the reference apparatus, are as follows:
  benzene: 16.6 t/h;
  toluene: 62 t/h;
  ethylbenzene: 12.5 t/h; and
  xylenes: 64.7 t/h;
  A9+: 55.9 t/h.

This gives a total of 211.7 t/h of aromatic compounds.

In the reference apparatus, the entirety of the toluene is converted into benzene and into xylenes by a transalkylating unit. The xylenes in the feedstock and produced by transalkylation are isomerized to para-xylene, which is separated from the xylenes mixture at the thermodynamic equilibrium at the exit of the isomerizing unit, by means of a simulated moving bed adsorption unit. This collective of unit operations allows production of the following compounds:
  benzene: 53 t/h;
  para-xylene: 145 t/h
  total aromatic: 198 t/h.

Inventive Apparatus Example

The inventive apparatus example allows both an increase in the total amount of aromatics produced, for the same feedstock flow rate as in the reference apparatus, and production only of the compound of greater added value: para-xylene.

The inventive apparatus example is similar to the apparatus represented in FIG. 1.

However, the inventive apparatus example does not employ the following units:
  selective hydrogenolysing unit 9; and
  stabilizing column 12.

Particular additions relative to the reference apparatus scheme are the alkylating reaction section 13 and the transalkylating reaction section 14, for alkylating the benzene with ethylene and for transalkylating the polyethylbenzenes to ethylbenzenes. The product of the transalkylation 14, namely the ethylbenzene, is introduced into the aromatic loop, which comprises the isomerizing unit 11, implemented with a liquid-phase isomerization reaction and a gaseous-phase isomerization reaction, and the xylenes separation unit 10.

According to the inventive apparatus example, and with the same feedstock entering the complex and the same yields of the unit operations as in the reference apparatus example, the performance data, by comparison with those for the reference apparatus, that are obtained are shown in table 1.

TABLE 1

|  | Reference apparatus example | Inventive apparatus example |
|---|---|---|
| Feedstock (t/h) | — | — |
| Ethylene | 0 | 19 |
| Benzene | 16.6 | 16.6 |
| Toluene | 62 | 62 |
| Ethylbenzene | 12.5 | 12.5 |
| Xylenes | 64.5 | 64.5 |
| A9+ | 55.9 | 55.9 |
| Products (t/h) | — | — |
| Benzene | 53 | 0 |
| p-Xylene | 145 | 217 |
| Total aromatics | 198 | 217 |

Table 1 shows that the implementation according to the invention enables production of 9.5 weight % of more aromatics (217 t/h rather than 198 t/h) and the production only of para-xylene, with an increase in para-xylene production of almost 50%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. An apparatus suitable for converting a feedstock (2) of aromatic compounds, comprising:
    a fractionating train (4-7) suitable for extracting at least one fraction comprising benzene (22), one fraction comprising toluene (23) and one fraction comprising xylenes and ethylbenzene (24) from the feedstock (2);
    a xylene separating unit (10) suitable for treating the fraction comprising xylenes and ethylbenzene (24) and for producing an extract (39) comprising para-xylene and a raffinate (40) comprising ortho-xylene, meta-xylene and ethylbenzene;
    an isomerizing unit (11) suitable for treating the raffinate (40) and producing a para-xylene-enriched isomerizate (42), which is sent to the fractionating train (4-7); and
    an alkylating reaction section (13) suitable for treating at least part of the fraction comprising benzene (22) with a source of ethylene (30) and producing an alkylating effluent (31) comprising ethylbenzene, which is sent to the isomerizing unit (11).

2. The apparatus according to claim 1, further comprising a transalkylating reaction section (14) suitable for transalkylating polyethylbenzenes present in the alkylation effluent (31) and producing an ethylbenzene-enriched fraction (32; 47).

3. The apparatus according to claim 1, further comprising a fractionating unit (15) suitable for treating the alkylation effluent (31) and producing a plurality of fractionation fractions comprising at least one ethylbenzene fraction (33), which is sent to the isomerizing unit (11), and one benzene fraction (35).

4. The apparatus according to claim 3, wherein the fractioning unit (15) is disposed downstream of the transalkylating reaction section (14) and is suitable for treating the ethylbenzene-enriched fraction (32; 47).

5. The apparatus according to claim 3, wherein the fractionating unit (15) is suitable for producing additionally at least one polyethylbenzene fraction (36), and wherein the transalkylating reaction section (14) is disposed downstream of the fractionating unit (15) and is suitable for treating at least part of said polyethylbenzene fraction (36).

6. The apparatus according to claim 1, wherein the fractionating train (4-7) is suitable for extracting a C9-C10 monoaromatics fraction (25) from the feedstock (2).

7. The apparatus according to claim 6, further comprising a transalkylating unit (8) suitable for treating the C9-C10 monoaromatics fraction (25) with the fraction comprising toluene (23) and producing xylenes, which are sent to the fractionating train (4-7).

8. The apparatus according to claim 1, further comprising a disproportionating unit (48) suitable for treating the fraction comprising toluene (23) and producing a xylene-enriched fraction (50), which is recycled to the isomerizing unit (11).

9. A process converting a feedstock (2) of aromatic compounds, comprising:
    fractionating the feedstock in a fractionating train (4-7) to extract at least one fraction comprising benzene (22), one the fraction comprising toluene (23) and one fraction comprising xylenes and ethylbenzene (24);
    separating the fraction comprising xylenes and ethylbenzene (24) in a xylene separating unit (10) and producing a para-xylene-comprising extract (39) and a raffinate (40) comprising ortho-xylene, meta-xylene and ethylbenzene;
    isomerizing the raffinate (40) in an isomerizing unit (11) and producing a para-xylene-enriched isomerizate (42);
    sending the para-xylene-enriched isomerizate (42) to the fractionating train (4-7);
    alkylating at least part of the fraction comprising benzene (22) with a source of ethylene (30) in an alkylating reaction section (13) and producing an alkylation effluent (31) comprising ethylbenzene; and
    sending the alkylation effluent (31) comprising ethylbenzene to the isomerizing unit (11).

10. The process according to claim 9, wherein the alkylating reaction section (13) comprises at least one alkylation reactor, which is used under the following operating conditions:
    temperature of between 20° C. and 400° C.;
    pressure of between 1 and 10 MPa;
    molar benzene/ethylene ratio of between 2 and 10;
    WWH of between 0.5 and 50 $h^{-1}$.

11. The process according to claim 10, wherein the alkylation reactor is operated in the presence of a catalyst comprising a zeolite.

12. The process according to claim 9, wherein the isomerizing unit (11) comprises a gas-phase isomerization zone and/or a liquid-phase isomerization zone, wherein the gas-phase isomerization zone is used under the following operating conditions:
    temperature of greater than 300° C.;
    pressure of less than 4.0 MPa;
    hourly space velocity (HSV) of less than 10 $h^{-1}$;
    molar hydrogen-to-hydrocarbon ratio of less than 10;

in the presence of a catalyst comprising at least one zeolite having channels whose opening is defined by a ring of 10 or 12 oxygen atoms, and at least one group VIII metal in an amount of between 0.1 and 0.3 weight %, endpoints included, and wherein the liquid-phase isomerization zone is used under the following operating conditions:

temperature of less than 300 C;

pressure of less than 4 MPa;

hourly space velocity (HSV) of less than 10 $h^{-1}$;

in the presence of a catalyst comprising at least one zeolite having channels whose opening is defined by a ring of 10 or 12 oxygen atoms.

13. The process according to claim 9, further comprising:

transalkylating polyethylbenzenes present in the alkylation effluent (31) in a transalkylating reaction section (14) and producing an ethylbenzene-enriched fraction (32; 47), and sending the ethylbenzene-enriched fraction (32; 47) to the isomerizing unit (11).

14. The process according to claim 13, wherein the transalkylating reaction section (14) comprises at least one transalkylation reactor, which is used under the following operating conditions:

temperature of between 200° C. and 400° C.;

pressure of between 1 and 6 MPa;

WWH of between 0.5 and 5 $h^{-1}$.

15. The process according to claim 14, wherein the transalkylation reactor (14) is operated in the presence of a catalyst comprising a zeolite.

\* \* \* \* \*